United States Patent
Shoshani et al.

(10) Patent No.: US 10,070,815 B2
(45) Date of Patent: *Sep. 11, 2018

(54) VERTICAL CONDUCTIVE TEXTILE TRACES AND METHODS OF KNITTING THEREOF

(71) Applicant: Healthwatch LTD., Herzeliya (IL)

(72) Inventors: Boaz Shoshani, Raanana (IL); Renen Ben David, Petah-Tikva (IL)

(73) Assignee: Healthwatch LTD., Herzeliya (IL)

( * ) Notice: Subject to any disclaimer, the term of this patent is extended or adjusted under 35 U.S.C. 154(b) by 526 days.

This patent is subject to a terminal disclaimer.

(21) Appl. No.: 14/646,971

(22) PCT Filed: Nov. 23, 2013

(86) PCT No.: PCT/IL2013/050963
§ 371 (c)(1),
(2) Date: May 22, 2015

(87) PCT Pub. No.: WO2014/080403
PCT Pub. Date: May 30, 2014

(65) Prior Publication Data
US 2015/0305676 A1 Oct. 29, 2015

Related U.S. Application Data

(60) Provisional application No. 61/729,549, filed on Nov. 24, 2012.

(51) Int. Cl.
| | |
|---|---|
| *A61B 5/00* | (2006.01) |
| *A61B 5/04* | (2006.01) |
| *D04B 1/14* | (2006.01) |
| *G06F 1/16* | (2006.01) |
| *D04B 1/24* | (2006.01) |
| *A61B 5/0408* | (2006.01) |

(Continued)

(52) U.S. Cl.
CPC .......... *A61B 5/6804* (2013.01); *A61B 5/6805* (2013.01); *D04B 1/14* (2013.01);
(Continued)

(58) Field of Classification Search
CPC .............. A41D 13/1281; A61B 5/0408; A61B 5/04085; A61B 5/6804; A61B 5/6805; D10B 2403/02431
(Continued)

(56) References Cited

U.S. PATENT DOCUMENTS

| | | |
|---|---|---|
| 7,849,888 B2 | 12/2010 | Karayianni et al. |
| 8,032,199 B2 | 10/2011 | Linti et al. |

(Continued)

FOREIGN PATENT DOCUMENTS

| | | |
|---|---|---|
| CN | 102247135 A | 11/2011 |
| WO | 2012104826 A1 | 8/2012 |

OTHER PUBLICATIONS

Santoni Spa—Santoni Products—Machines. Restreived from: http://www.santoni.com/en-prodotti.asp on Jun. 22, 2018.*

(Continued)

*Primary Examiner* — Christopher D Koharski
*Assistant Examiner* — Pamela M Bays
(74) *Attorney, Agent, or Firm* — Troutman Sanders LLP

(57) ABSTRACT

A method for knitting a garment having a tubular form, including knitting at least one vertical conductive textile trace on a machine having N participating feeders and M needles. The method includes the steps of continuously knitting the tubular form with one or more flexible non-conductive base yarns, and knitting the vertical conductive textile trace integrally within the tubular form, using a conductive yarn, in addition to spandex yarns, but not the base yarns. The conductive yarn is knitted in a float-loop form by knitting a stitch and skipping over y needles, as follows: repeatably knitting a line segment $L_k$, using feeder $F_i$ and starting at needle $D_1$; and knitting line segment $L_{k+1}$, using the next feeder and start stitching the first float-loop at needle $D_1+s$ where $0<s<y$.

16 Claims, 2 Drawing Sheets

(51) Int. Cl.
 A41D 13/12 (2006.01)
 D04B 1/16 (2006.01)
(52) U.S. Cl.
 CPC ............... *D04B 1/24* (2013.01); *G06F 1/163* (2013.01); *A41D 13/1281* (2013.01); *A61B 5/0408* (2013.01); *A61B 5/04012* (2013.01); *A61B 5/04085* (2013.01); *A61B 2562/0209* (2013.01); *A61B 2562/125* (2013.01); *D04B 1/16* (2013.01); *D10B 2401/18* (2013.01); *D10B 2403/02431* (2013.01)
(58) Field of Classification Search
 USPC ........................................................ 600/388
 See application file for complete search history.

(56) References Cited

U.S. PATENT DOCUMENTS

| | | | |
|---|---|---|---|
| 8,171,755 B2 | 5/2012 | Jahn et al. | |
| 2006/0281382 A1* | 12/2006 | Karayianni | .......... D03D 1/0088 442/181 |
| 2008/0287022 A1 | 11/2008 | Dhawan et al. | |
| 2009/0018428 A1* | 1/2009 | Dias | ................... A41D 13/1281 600/388 |
| 2010/0208445 A1 | 8/2010 | Asvadi et al. | |
| 2011/0259638 A1 | 10/2011 | Sherrill et al. | |

OTHER PUBLICATIONS

Santoni SPA—Santoni Products—Machines. Retrieved from http://www.santoni.com/en-prodotti.asp on Jun. 22, 2018.*
International Search Report for PCT/IL2013/050963 dated Mar. 23, 2014.
Spencer, David J., Knitting Technology: A Comprehensive Handbook and Practical Guide, vol. 16 of Woodhead Publishing Series in Textiles, CRC Press, 2001, 9.4 The Float Stitch (p. 92), ISBN 1587161214.
Niir Board, The Complete Technology Book on Textile Spinning, Weaving, Finishing and Printing, National Institute of Industrial Re, 2009, p. 251—float loop, ISBN 8178330490.

* cited by examiner

VERTICAL CONDUCTIVE TEXTILE TRACES AND METHODS OF KNITTING THEREOF

CROSS REFERENCE TO RELATED APPLICATIONS

This application claims the benefit under 35 USC 119(e) from U.S. provisional application No. 61/729,549 filed Nov. 24, 2012, the disclosures of which is included herein by reference.

FIELD OF THE INVENTION

The present invention relates to real-time health monitoring systems and more particularly, the present invention relates to vertical conductive traces embedded into a knitted garment having a tubular form at preconfigured locations, transferring ECG or other signals from textile electrodes to a selected area of the garment.

BACKGROUND OF THE INVENTION AND PRIOR ART

Monitoring systems for monitoring of physiological parameters of a living being are well known in prior art. For example, PCT/IL2010/000774, the disclosure of which is included herein by reference in its entirety, discloses a health monitoring system that continuously checks the wellbeing of a person (or any other living being) that, typically, is considered healthy (or with a known set of diseases), covering a significant range of health hazards that may cause a significant life style change/limitation, and provides an alert as early as possible—all this, with no significant limitation to the normal life style of the person bearing the system.

Unlike conventional gel electrodes, which are directly applied to the living being's skin, using a conductive gel, textile electrodes are dry contact sensors adapted for use in measuring ECG signals and other vital signals such (EEG), electroencephalogram (EOG), electrooculogram and other medical measurements on the skin without any skin preparation, such as needed with wet electrodes, for example, shaving hairy skin.

To improve the performance of conventional wet ECG sensors and to be able to conduct continuous long term monitoring, a textile substrate is used to develop dry textile electrodes for sensing physiological parameters of a living being such as ECG signals. One such textile electrodes are disclosed in U.S. provisional application 61/729,548 filed Nov. 24, 2012, and in follow up applications depending thereon, such as PCT application PCT/IL2013/050963.

There is however a need to transfer the sensed electrical signals vertically along the knitted product and across knitted line segments, to a processing unit, preconfigured to process the sensed signal.

The term "seamless", as used herein with conjunction with a wearable device, refers to a device that when worn by an average person, wherein the device puts no significant limitation to the normal life style of that person and preferably not seen by anybody when used and not disturbingly felt by the user while wearing it. Furthermore, no activity is required from the monitored person in order for the system to provide a personal-alert when needed. It should be noted that people that pursue non-common life style, such as soldiers in combat zone or in combat training zone, or firefighters in training and action, or athletes in training or competition may utilize non-seamless devices. As the "seamless" characteristics refers also to the user's behavior, the wearable component is preferably an item that is normally worn (e.g., underwear) and not some additional item to be worn just for getting the alert.

The terms "underwear" or "garment", as used herein with conjunction with wearable clothing items, refers to seamless wearable clothing items that preferably, can be tightly worn adjacently to the body of a monitored living being, typically adjacently to the skin, including undershirts, sport shirts, brassiere, underpants, special hospital shirt, socks and the like. Typically, the terms "underwear" or "garment" refer to a clothing item that is worn adjacently to the external surface of the user's body, under external clothing or as the only clothing, in such way that the fact that there are sensors embedded therein, is not seen by any other person in regular daily behavior. An underwear item may also include a clothing item that is not underwear per se, but still is in direct and preferably tight contact with the skin, such as a T-shirt, sleeveless or sleeved shirts, sport-bra, tights, dancing-wear, and pants. The sensors, in such a case, can be embedded in such a way that are still unseen by external people to comply with the "seamless" requirement.

The terms "course" and "line segment", are used herein as related terms. The tubular form of the garment is knitted on a knitting machine, such as a Santoni knitting machine, where the tubular form is knitted in a spiral having substantially horizontal lines. A single spiral loop/circle us referred to herein as a course and a portion of a course is referred to as line segment.

The term "vertical conductive trace", is used herein, refers to knitting a lead wire, made of conductive yarns, and capable of transferring electrical signals across knitted line segment.

The phrase "clinical level ECG", as used herein with conjunction with ECG measurements, refers to the professionally acceptable number of leads, sensitivity and specificity needed for a definite conclusion by most cardiology physicians to suspect a risky cardiac problem (for example, arrhythmia, myocardial ischemia, heart failure) that require immediate further investigation or intervention. Currently, it is at least a 12-leads ECG and preferably 15-lead ECG, coupled with a motion/posture compensation element, and a real-time processor with adequate algorithms.

One of the main technical challenges in using dry textile electrodes that are knitted integrally with tubular form garments, used for sensing electric and other physiological parameters, is in transferring clinical level ECG and/or other sensed signals from the textile electrodes, along the knitted fabric, to a selected area, in particular between adjacent knitting courses in the vertical direction, where conductivity may be impaired.

There is therefore a need to develop conductive mean that are built into the knitted fabric as part of the fabrication of the garment, wherein the conductivity, in particular between adjacent knitting courses in the vertical direction, can support the transfer clinical level of ECG signal from a textile electrode, along the fabric, to a selected area in the garment preconfigured to host a processing unit.

The good conductivity should prevail when the fabric is stretched to different directions during wearing.

The good conductivity should prevail after a preconfigured number of washes, including in a washing machine.

The good conductivity should prevail in any knitting design, location and shape in the fabric, including in diagonal lines, with respect to the knitting course direction.

The good conductivity should prevail when using any type of basic fabric yarns (cotton, manmade yarns, synthetic yarns, etc.).

There is therefore a need and it would be advantageous to provide a knitting method for knitting vertical conductive traces embedded into a knitted garment having a tubular form at preconfigured locations, transferring ECG or other signals from textile electrodes to a selected area of the garment.

BRIEF SUMMARY OF THE INVENTION

In order to transfer the electrical signals vertically along the knitted product and across knitted line segments, this invention teaches a unique knitting structure that was developed using knitting machines for producing garments having a tubular form, such as a seamless Santoni knitting machine.

It should be noted that the signals can be any sensed electric signals (e.g. respiration) and it is not restricted to ECG signals. It should also be noted that any non-horizontal angle can be knitted using this invention by a continuous sequence of vertical lines.

Horizontal traces perform well the conductive yarn has a continuous conductive filament for the signal to flow through. In the at least partially vertical direction, the vertical conductive traces are composed of line segments knitted on top of one another and may also have a course of elastic, non-conductive yarn (e.g. Spandex), knitted in between the two line segments of conductive yarn. The conductive line segments may still have mutual contact, but when stretched they may be pulled apart to the point of reduced conductivity or no conductivity.

The main challenge is to get the two line segments of conductive yarn to always touch even when a course of elastic yarn is knitted in between them regardless of the stretch/pull of the garment during wearing.

According to teachings of the present invention, there is provided a method for knitting a garment having a tubular form being knitted with a base-yarn, including knitting at least one vertical conductive textile trace, using a knitting machine having N feeders and M needles. The base-yarn does not participate in the knitting of the conductive textile electrode. The method includes the steps of continuously knitting the tubular form with one or more flexible non-conductive yarns, and knitting the at least one textile electrode integrally within the tubular form, using a conductive yarn, in addition to a spandex yarn. The conductive yarn is knitted in a float-loop form by knitting a stitch and skipping over y needles, as follows:

i) knitting a line segment $L_k$, using feeder $F_i$ and start stitching with needle $D_j$, wherein typically, j=1;

ii) knitting line segment $L_{k+1}$, using feeder $F_{i+1}$ and start stitching the first float-loop with needle $D_j$+s, where 0<s<y; and iii) repeat steps (i) and (ii) for a preconfigured number of line segments, wherein each line segment has a preconfigured length.

BRIEF DESCRIPTION OF THE DRAWINGS

The present invention will become fully understood from the detailed description given herein below and the accompanying drawings, which are given by way of illustration and example only and thus not limitative of the present invention, and wherein.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided, so that this disclosure will be thorough and complete, and will fully convey the scope of the invention to those skilled in the art.

An embodiment is an example or implementation of the inventions. The various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments", "another embodiment" or "other embodiments" means that a particular feature, structure, or characteristic described in connection with the embodiments is included in at least one embodiments, but not necessarily all embodiments, of the inventions. It is understood that the phraseology and terminology employed herein is not to be construed as limiting and are for descriptive purpose only.

Methods of the present invention may be implemented by performing or completing manually, automatically, or a combination thereof, selected steps or tasks. The term "method" refers to manners, means, techniques and procedures for accomplishing a given task including, but not limited to, those manners, means, techniques and procedures either known to, or readily developed from known manners, means, techniques and procedures by practitioners of the art to which the invention belongs. The descriptions, examples, methods and materials presented in the claims and the specification are not to be construed as limiting but rather as illustrative only.

It should be noted that orientation related descriptions such as "bottom", "up", "horizontal", "vertical", "lower", "top" and the like, assumes that the is worn by a person being in a standing position.

Meanings of technical and scientific terms used herein are to be commonly understood as to which the invention belongs, unless otherwise defined. The present invention can be implemented in the testing or practice with methods and materials equivalent or similar to those described herein.

Figure 1B:
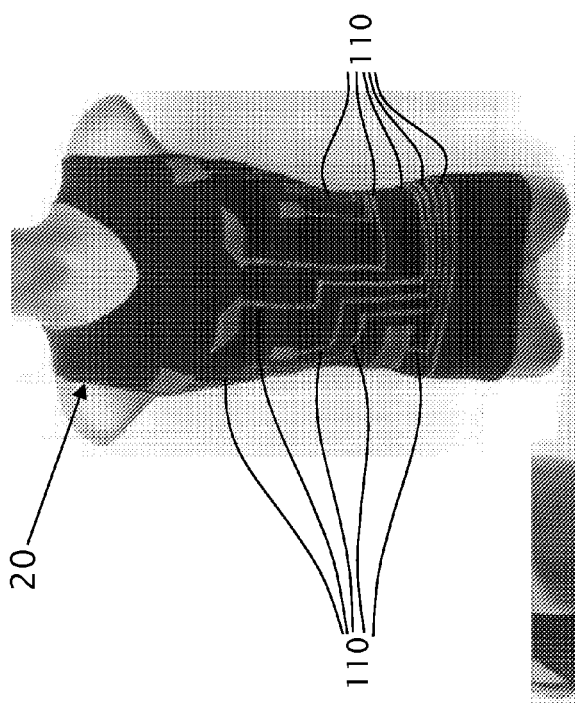
FIG. 1b depicts a front view of an exemplary garment, wherein the textile electrodes are designed to measure a 15-lead ECG signal.
Figure 1C:
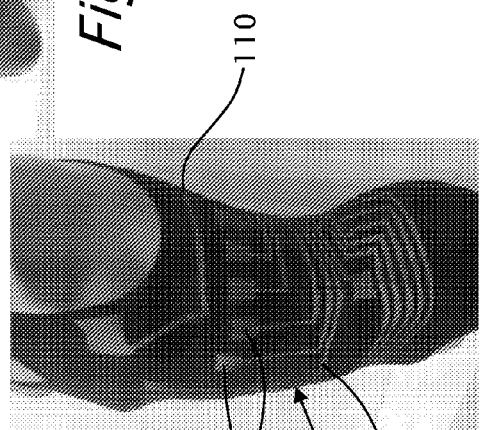
FIG. 1c depicts a side view of the garment shown in FIG. 1b.
Figure 1A:
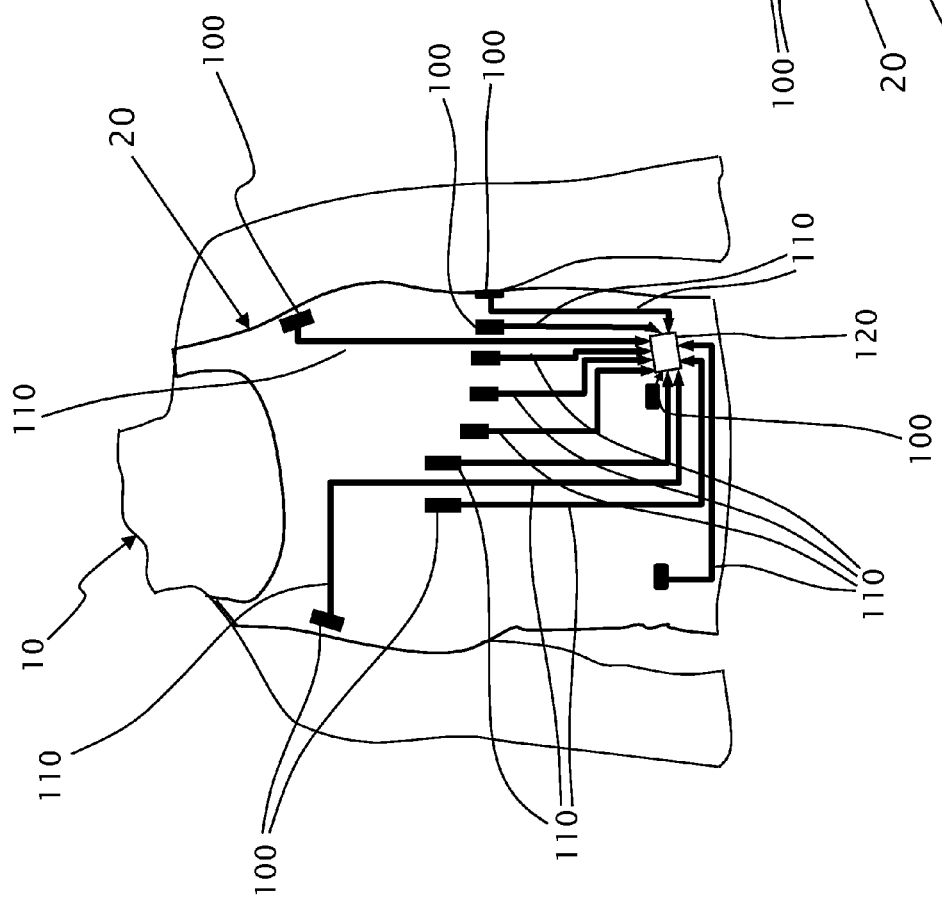
FIG. 1a is a schematic illustration of an exemplary garment, having a tubular form, wherein textile electrodes, according to embodiments of the present invention, are knitted therein.

FIG. 1a is a schematic illustration of an exemplary knitted smart garment 20, according to embodiments of the present invention, having knitted dry textile electrodes 100, wherein typically, textile electrodes 100 are interconnect with a processor 120 by conductive means 110. Smart garment 20 is knitted, with no limitations, on a circular seamless knitting machine, such as a Santoni knitting machine. The fabric can be knitted, with no limitations, on a 24 gauge or 28 gauge machine (number of needles per inch) and in a wide range of diameters such as 17", 18" and 20", according to the final size and dimensions of the finished garment product. FIG. 1b depicts a front view of an exemplary garment 20, wherein the textile electrodes 100 are designed to measure a 15-lead ECG signal; and FIG. 1c depicts a side view of the garment shown in FIG. 1b.

In one example embodiment, with no limitations, the fabric is knitted with Nylon, bare Spandex and covered spandex. In another example embodiment, the fabric is knitted using Nylon and covered spandex. In one example embodiment, with no limitations, the conductive yarn used to knit the conductive traces 110 is Nylon coated with Silver by Xstatic.

It should mention that such a garment can be knitted with any type of Nylon yarn textured or flat, selected types of Nylons, Polyester, Acetate, manmade fibers, natural yarns like cotton, bamboo, wool, and blends of the mentioned raw materials. Selection of yarn is also based on fabric weight, body size for men and women, fabric weight and design required.

It is also to be mentioned that such a garment can be knitted on any given machine gauge or diameter based on the fabric weight, size, and design required.

The thickness (Den or Dtex) of the basic yarns to knit the garment and type of Spandex yarn used should be in line with the machine gauge and type of fabric requested.

It should be noted that the term "ECG signals", as used herein, refers the any physiological signals of the monitored living being, including signals for ECG analysis.

The knitted electrodes are located in the selected areas on the fabric based on the desired ECG signals efficiency. Each electrode is connected to conductive lead wire (trace) 110 which preferably, is knitted with same conductive yarn of the electrodes 100. The knitted conductive leads 110 are delivering the ECG signals sensed by the knitted electrodes to a specific area on the garment, were all the conductive leads are gathering to deliver the signals to the ECG processing device 120.

The conductive lead wire (trace) 110 are knitted to form float loops made of the conductive yarns (for example, 70/2 Den by Xstatic), which are designed to float over the fabric surface in the number of needles as designed. The length of the float loop is determines by the number of needles the loop if floating over.

As described in this invention the length of the float loops, as well as the specific knitting density in the conductive traces 110 area, and in selected areas in the basic garment, is determined by the desired quality level of ECG signals.

In this invention the use of float loops in a shifted needle knitting scheme, together with unique digital knitting density control, enables achieving good conductivity across knitting courses.

Figure 2:
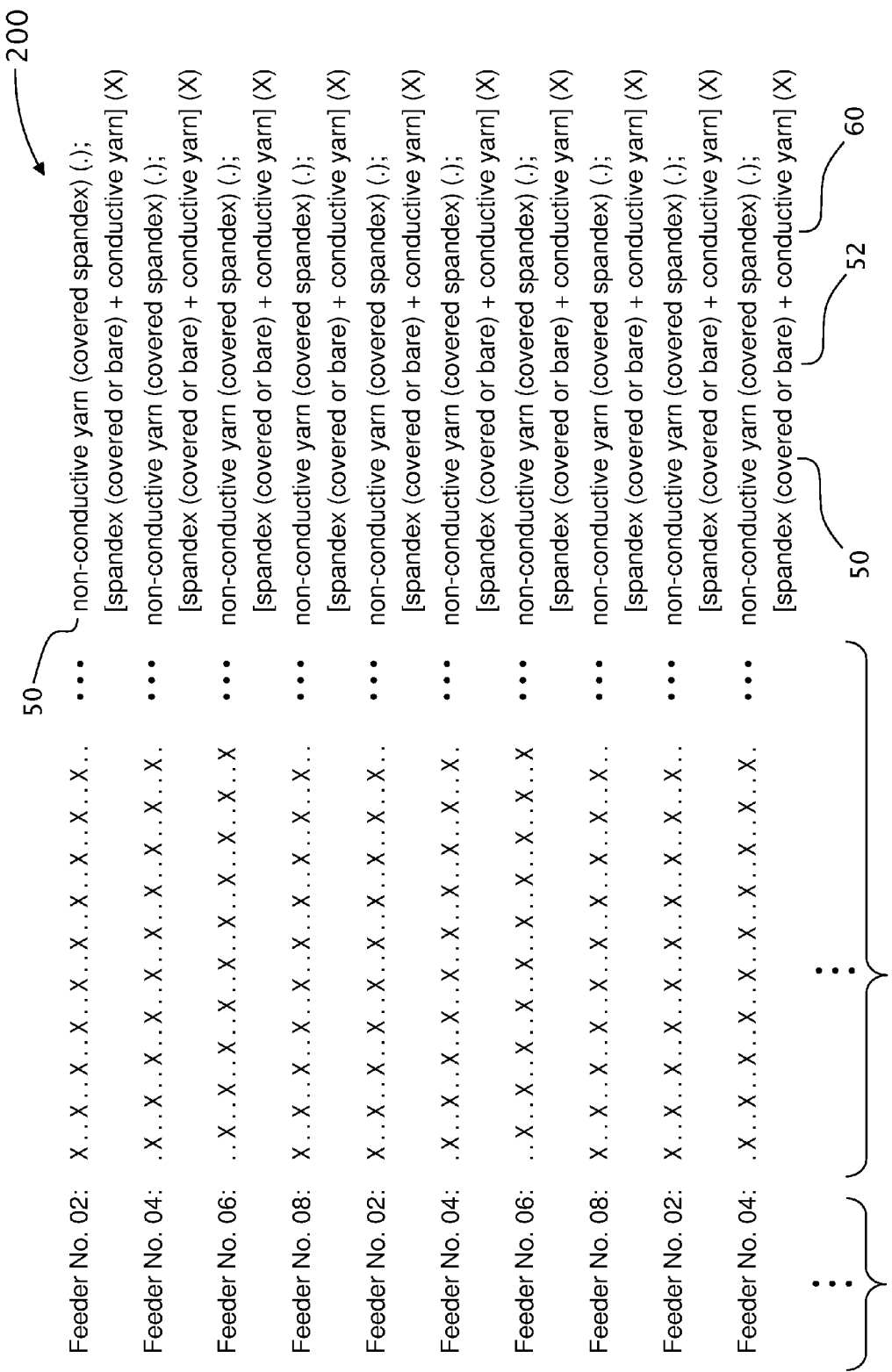
FIG. 2 is an example knitting scheme of a conductive electrode designed for a Santoni type knitting machine, according to embodiments of the present invention, wherein the float loop is made of a conductive yarn made of Nylon covered with silver, knitted together with covered Spandex and bare spandex, wherein the float-loops are knitted in a shifted float-loop design to improve the knitting density and pressure of the electrode on the body.

The conductive lead wires 110 are knitted together in same knitting process of knitting the basic garment and preferably, with no limitations, same knitting process of the electrodes, and coming out the machine as one single unit of a tubular form. FIG. 2 describes an example knitting method 200 of producing a float-loop conductive trace 110, according to embodiments of the present invention. The conductive trace 110 is fabricated on a Santoni type knitting machine, wherein the float loop is made of a conductive yarn made of Nylon covered with silver, knitted together with covered Spandex and bare spandex, wherein the float-loops are knitted in a shifted float-loop design to improve the knitting density and thereby improve conductivity.

FIG. 2 schematically illustrating example knitting scheme 400 of a float-loop conductive trace 110, designed for a 4 (four) feeds system, but using in the example, with no limitations, an 8 feed Santoni type knitting machine, according to some embodiments of the present invention.

In this embodiment, in all the knitting courses, the float loops that are formed from a conductive yarn 60 (such as Xstatic), that float over 2 needles, as can be seen and appreciated by a person skilled in the art in FIG. 2, while the non-conductive covered (or bared) spandex 50 (or 52) is knitted continuously in the same knitted course. It should be noted that, in this embodiment, the base-yarn of the garment does not participate in the knitting of the float-loop conductive trace 110.

In the example shown in FIG. 2, only four out of eight available feeders are used: feeders 1, 3, 5 and 7 are not used while feeders 2, 4, 6 and 8 are used. The same knitting scheme 440 is used in all courses. However, the float-loop stitch starting needle $D_j$ in Feeder i+2 is shifted by s4 needles with respect to the float-loop stitch starting needle in Feeder i. In the example shown in FIG. 4, s4=1.

The present invention is not limited to the knitting parameters shown in the examples as illustrated in FIG. 2 and corresponding description in the specifications. The examples as illustrated in FIG. 2 exemplifies methods for knitting a garment 20 having a tubular form, including knitting at least one float-loop conductive trace 110 electrically connecting an electrode such as conductive textile electrode 100, to a processing unit 120.

In one embodiment the method includes continuously knitting a tubular form 20 with a flexible non-conductive yarn 50 and/or 52, knitting the at least one float-loop conductive trace 110 integrally within tubular form 20, using a conductive yarn 60, in addition to a spandex yarn. The conductive yarn 60 is knitted in a float-loop form by knitting a stitch and then skipping over y needles, as follows:
  i) knitting a course k, being a line segment $L_k$, using feeder $F_i$ and starting at needle $D_j$, wherein the next float-loop starting stitch is at y needles away from the starting stitch needle of the previous float-loop;
  ii) knitting line segment $L_{k+1}$, using the next participating feeder and starting stitching the first float-loop with needle $D_{j+s}$, where 0<s<y and typically, j=1; and
  iii) repeat steps (i) and (ii) for a preconfigured length of the tubular form 20, i.e. a preconfigured number of knitting courses.

It should be noted that each line segment has a preconfigured length.

It should be further noted that a preconfigured number of feeders of the knitting machine participate in the knitting process of the garment.

It should be further noted that vertical conductive traces 110 can be knitted with various conductive yarn dtex and various number of filaments and on various gauge knitting machines.

It should be further noted that vertical conductive traces 110 can be knitted also in a diagonal form, when needed.

The invention being thus described in terms of embodiments and examples, it will be obvious that the same may be varied in many ways. Such variations are not to be regarded as a departure from the spirit and scope of the invention, and all such modifications as would be obvious to one skilled in the art are intended to be included within the scope of the claims.

What is claimed is:

1. A knitted smart garment for monitoring a living being, the garment comprising:
 a) a sensing device for sensing an electrical vital signal of the monitored living being;
 b) a tubular form having a first multiplicity of knitted lines, wherein each said line is knitted with at least one flexible, non-conductive yarn; and
 c) at least one conductive vertical textile trace adapted to transmit said electrical vital signal vertically across conductive line segments to a target electric device, said at least one conductive vertical textile trace has a second multiplicity of vertically-aligned adjacent knitted line segments, wherein each of said knitted line segments is knitted within said knitted lines with at least one flexible, non-conductive yarn and a conductive yarn, and wherein each of said knitted line segments has a third multiplicity of float loops, wherein said third multiplicity of float loops is configured to provide the conductivity needed across said second multiplicity of knitted line segments, to further transmit a received electrical vital signal from said sensing device to said target electric device,
  wherein a first float loop in a first line segment of said knitted line segments begins in a given stitching position, and wherein an immediately-subsequent float loop in each subsequent said line segment is vertically aligned in a shifting position with respect to an immediately-preceding said line segment;
  wherein said shifting position is at least one needle position; and
  wherein said at least one conductive vertical textile trace is insulated from skin of the monitored living being.

2. The garment of claim 1, wherein said electrical vital signal is a clinical-level ECG signal.

3. The garment of claim 1, wherein said target electric device is a processing unit.

4. The garment of claim 1, wherein said shifting position is less than half of the number of skipped needle positions of each said float loop.

5. The garment of claim 1, wherein said shifting position is adapted to create a suitable knitting density of said third multiplicity of float loops, and wherein said suitable knitting density is adapted to provide enhanced electrical conductivity, vertically, across said second multiplicity of knitted line segments.

6. The garment of claim 1, wherein said at least one conductive vertical textile trace is knitted with a density that is adapted to sustain good conductivity when said tubular form is stretched vertically.

7. The garment of claim 1, wherein said sensing device is an electrode.

8. The garment of claim 1, wherein said sensing device is a textile electrode.

9. A method for knitting a smart garment configured to monitor a living being, the method comprising the steps of:
 a) knitting a tubular form having a first multiplicity of knitted lines, and wherein each said line is knitted with at least one non-conductive yarn; and
 b) knitting at least one conductive vertical textile trace for transferring an electrical vital signal from a sensing device to a target electric device, wherein said at least one conductive vertical textile trace has:
  i. a second multiplicity of vertically-aligned adjacent knitted line segments, wherein each of said knitted line segments is knitted within said knitted lines with a non-conductive yarn and a conductive yarn; and
  ii. a third multiplicity of float loops, wherein said third multiplicity of float loops is configured to provide the conductivity needed, across said second multiplicity of knitted line segments, to further transmit a received electrical vital signal from said sensing device to said target electric device,
 wherein a first float loop in a first line segment of said knitted line segments begins in a given stitching position, and wherein an immediately-subsequent float loop in each subsequent said line segment is vertically aligned in a shifting position with respect to an immediately-preceding said line segment;
 wherein said shifting position is at least one needle position; and
 wherein said at least one conductive vertical textile trace is insulated from skin of the monitored living being.

10. The method of claim 9, wherein said electrical vital signal is a clinical-level ECG signal.

11. The method of claim 9, wherein said target electric device is a processing unit.

12. The method of claim 9, wherein said shifting position is less than half the number of skipped needle positions of each said float loop.

13. The method of claim 9, wherein said shifting position is adapted to create a suitable knitting density of said third multiplicity of float loops, and wherein said suitable knitting density is adapted to provide enhanced electrical conductivity across said second multiplicity of knitted line segments.

14. The method of claim 9, wherein said at least one conductive vertical textile trace is knitted with a density that is adapted to sustain good conductivity when said tubular form is stretched vertically.

15. The method of claim 9, wherein said sensing device is an electrode.

16. The method of claim 9, wherein said sensing device is a textile electrode.

* * * * *